United States Patent [19]

Erdmann et al.

[11] 4,049,379

[45] Sept. 20, 1977

[54] COMPLEX BASIC ZIRCONIUM SALTS AND ALUMINUM SALTS

[75] Inventors: Hans Erdmann, Heidelberg; Franz-Friedrich Miller, Ludwigshafen, both of Germany

[73] Assignee: BASF Aktiengesellschaft, Ludwigshafen (Rhine), Germany

[21] Appl. No.: 706,765

[22] Filed: July 19, 1976

Related U.S. Application Data

[62] Division of Ser. No. 579,885, May 22, 1975.

[30] Foreign Application Priority Data

May 30, 1974 Germany .............................. 2425970

[51] Int. Cl.$^2$ ................................................ C14C 3/02
[52] U.S. Cl. ...................................... 8/94.26; 8/94.29
[58] Field of Search ............................... 8/94.26, 94.29

[56] References Cited

U.S. PATENT DOCUMENTS

| | | | |
|---|---|---|---|
| 2,264,414 | 12/1941 | Somerville et al. | 8/94.26 |
| 2,316,141 | 4/1943 | Wainer | 260/429.3 |
| 2,498,514 | 2/1950 | Van Mater | 260/429.3 X |
| 2,502,411 | 4/1950 | Neher et al. | 260/429.3 X |
| 3,104,248 | 9/1963 | Clearfield | 260/429.3 |
| 3,296,242 | 1/1967 | Turner et al. | 260/429.3 X |
| 3,405,153 | 10/1968 | Jones | 260/429.3 |
| 3,407,254 | 10/1968 | Siegal et al. | 260/429.3 X |
| 3,423,162 | 1/1969 | Papayannis et al. | 8/94.25 |
| 3,553,316 | 1/1971 | Rubino | 260;424/439.3 X;68 |
| 3,792,068 | 2/1974 | Luedders et al. | 260/429.3 |
| 3,792,976 | 2/1974 | Erdmann et al. | 8/94.26 |
| 3,870,464 | 3/1975 | Briggs | 8/94.26 |

FOREIGN PATENT DOCUMENTS 1,353,086  1/1964  France

*Primary Examiner*—John Kight, III
*Attorney, Agent, or Firm*—Keil, Thompson & Shurtleff

[57] ABSTRACT

New complex salts with zirconium and aluminum as central atoms and oxo, hydroxy, organic acido and sulfato groups as ligands, and a process for tanning skins and hides with these complex salts as tanning materials.

10 Claims, No Drawings

COMPLEX BASIC ZIRCONIUM SALTS AND ALUMINUM SALTS

This is a division of application Ser. No. 579,885 filed May 22, 1975.

The use of zirconium tanning materials and aluminum tanning materials is known. (F. Stather, Gerbereichemie and Gerbereitechnologie, Akademie-Verlag Berlin 1957, pages 468–473 and pages 481–482). The advantages of these tanning materials over the chrome tanning materials used almost exclusively at the present time is that they give white leather which can be dyed in substantially more brilliant hues then green chrome leather and also that they do not involve any effluent problems, whilst such problems make it doubtful whether chrome tanning can be sustained in the longer term.

The reasons why zirconium tanning materials and aluminum tanning materials have, in spite of these advantages, not found significant acceptance as sole tanning materials in the tanning industry reside in the severe disadvantages from which these types of tannage suffer. Zirconium leather and aluminum leather do not have the handle of chrome leather and in particular they are not boil-resistant, that is to say the leather tanned with these materials does not withstand 1 minute's residence in boiling water. Detanning and severe shrinkage of the hide occur, making it impossible, e.g., to dye such leathers at elevated temperatures.

It is an object of the present invention to provide combinations of zirconium tanning materials and aluminum tanning materials which in addition to having the known advantageous properties of such agents approach the previously superior quality of a chrome leather in respect of handle and boil resistance. Hitherto, the achievement of this object has required using these tanning materials in combination with other types of tannage. Since the previously known combination with chrome tanning materials is not relevant to the object of the invention because it perpetuates the problems of effluent contamination and discoloration, all that remained was a combination with aldehydes which, when using certain masking agents on the mineral tanning material, at least gives boil-resistant leather. Such combination tannage with aldehydes, however, is not yet an ideal practical solution, because, apart from the expense of two successive tannage processes, the leather at times suffers a reduction in tear strength and becomes waterabsorbent.

It is therefore an object of the present invention to provide pure mineral tanning materials which can be employed without resorting to combination with other tanning materials, such as chrome tanning materials, and which give white leather with a handle and boil resistance comparable to a chrome leather.

This object is achieved because of the surprising discovery that zirconium salts and aluminum salts, when used as tanning materials under certain conditions, give boil-resistant leathers, though these metal components, employed as individual tanning materials, do not give boil-resistant leather. The requisite conditions, which are explained in detail later, include selected weight ratios of the metal components, adequate masking and rendering the mixture basic.

The invention provides novel complex salts which contain zirconium and aluminum as central atoms and oxy, organic acido, sulfato and possibly hydroxy groups as ligands. Chloro groups may also be present as ligands if they are introduced into the system through the aluminum salts used.

The new complex salts have the empirical formula $$[(ZrO)_a(Al)_b(OH)_c(R)_d(X)_f] H_e$$

in which R is a monocarboxylic acid radical of 1 to 4 carbon atoms, X is chloride or half of sulfate, $a$ is from 1 to 9, preferably from 4 to 9, and $b$ is from 1 to 9, preferably from 1 to 6, $c$ is from 0 to $((4a+3b)-0.333(a+b))$, preferably from 0 to $(3a+2b)$ and $d$ is from $0.333(a+b)$ to $((4a+3b)-0.333(a+b))$, preferably from $0.333(a+b)$ to $(3a+2b)$, provided $c+d$ is from $0.333(a+b)$ to $(4a+3b)$, preferably $(3a+2b)$, and $f$ is $(4a+3b)-(c+d)$ and $e$ is $2a$.

The general formula is an empirical formula; accordingly, the indices $a$ to $f$ in the formula are the molar ratio of the atoms and groups of atoms to one another, in the new complex salts, but not necessarily the actual number of these atoms and groups of atoms in one molecule. The actual molecular size of the complex salts depends on external factors, especially on the pH, concentration and temperature of the solutions.

The monocarboxylic acid radicals are derived from saturated or unsaturated monocarboxylic acids of 1 to 4 carbon atoms, e.g. from formic acid, acetic acid, propionic acid, lactic acid, acrylic acid or methyacrylic acid. Industrially, propionic acid is of particular interest.

The complex compounds are tanning materials which give leather having a fully satisfactory handle.

Using the preferred molar ratios of the components, the compounds are particularly readily water-soluble. The solubility decreases with increasing values of $c$ and $d$ so that the stated limiting values are only achieved at very high dilutions. The products of the invention only achieve their maximum tanning efficiency when the relation $c + d = 4a + 3b$ is observed and the proportion of monocarboxylic acid groups is at least 0.333 mole of acid radical/1 mole of metal. It is therefore expedient to start from the readily water-soluble compounds of low complex loading and introduce the amount of carboxylic acid radicals or alakli still lacking if optimum tannage is to be achieved, by mixture to the product or by use in neutralizing the tanning liquor at the end of the tannage. This is equivalent to saying that the complexes according to the invention can also be produced during tanning in which case the tanning effect is completed after addition of the residual amounts of acid radicals or of alkali. To keep the proportion of neutral salt in the product at a low level, sulfate may be precipitated with calcium hydroxide or organic acid radicals may be added in the form of the corresponding calcium salts.

The range of the molar ratio of the two metals stated to be preferred comprises the complex salts which, when employed as tanning materials, give particularly boil-resistant leathers.

The invention further provides the use of the new complex salts as white tanning materials, especially for boilresistant leathers.

Examples of the complex salts formed according to the invention are:

| ((ZrO)) | Al | $(OH)_{2.25}$ | $(R)_{2.25}$ | $(X)_{2.5)}$ | $H_2$ |
|---|---|---|---|---|---|
| ((ZrO)) | Al | $(OH)_{3.833}$ | $(R)_{0.666}$ | $(X)_{2.5)}$ | $H_2$ |
| ((ZrO)) | Al | $(OH)_{0.666}$ | $(R)_{3.833}$ | $(X)_{2.5)}$ | $H_2$ |
| ((ZrO)) | $Al_9$ | $(OH)_{10}$ | $(R)_{10}$ | $(X)_{11)}$ | $H_2$ |
| ((ZrO)) | $Al_9$ | $(OH)_{16.66}$ | $(R)_{3.33}$ | $(X)_{11)}$ | $H_2$ |
| ((ZrO)) | $Al_9$ | $(OH)_{3.33}$ | $(R)_{16.66}$ | $(X)_{11)}$ | $H_2$ |

-continued

| ((ZrO) | Al | (OH)₁₄ | (R)₁₄ | (X)₁₁) | H₁₈ |
| ((ZrO)₁.₅ | Al | (OH)₃ | (R)₃ | (X)₃) | H₃ | wherein R and X have the meaning defined above.

These empirical formulae do not indicate whether water or sodium sulfate or sodium chloride are eliminated from the metal complex in the course of the reaction. These components are immaterial to the tanning effect achieved.

The salts of the invention may be prepared on various ways.

An advantageous starting material for the zirconium constituent in these complex salts is 50%-basic zirconium sulfate which is known to exist as monooxo-disulfato-zirconium-acid, which will here be referred to, for simplicity, as zirconylsulfuric acid, and which has the formula $$(ZrO(SO_4)_2)H_2$$

In principle, the compound $(Zr(SO_4)_4)H_4$ may also be used as a starting material, but because of the inadequate stability of this acid it is expedient to convert it to the more stable zirconylsulfuric acid.

Zirconylsulfuric acid may be reacted with alkali metal salts of organic acids, or with such alkali metal salts and alkaline reagents such as alkali metal hydroxide or alkali metal carbonate, giving complex basic acido-sulfato-zirconium salts. Examples of such salts which may be reacted further are:

| (ZrO R | (SO₄)₁.₅) | H₂ | (ZrO₁.₅ | R | (SO₄)) | H₂ |
| (ZrO R₂ | (SO₄)) | H₂ | (ZrO₁.₅ | R₂ | (SO₄)₀.₅) | H₂ |
| (ZrO R₃ | (SO₄)₀.₅) | H₂ | (ZrO₂ | R | (SO₄)₀.₅) | H₂ |

Particularly suitable starting materials for providing the aluminum constituent in the products according to the invention are aluminum cloride and aluminum sulfate, alum and their reaction products with alkali metal salts of the organic acids or the alkali metal salts together with further alkaline reagents. The latter in particular include sodium or potassium compounds, such as hydroxides or carbonates, preferably the sodium compounds. In the text which follows these will be referred to as "alkalis"0 or be denoted by the prefix "alkali". Magnesium hydroxide, carbonate and oxide, and calcium hydroxide, carbonate and oxide are further suitable alkaline reagents. In many cases, dolomite $(MgCO_3 \times CaCO_3)$ is used as a slow-acting alkaline reagent. Examples of such aluminum salts, which may be used for further conversion, are:

| Al | (SO₄)₁.₅ | or Cl₃ | Al | R₁.₅ | (SO₄)₀.₇₅ | or Cl₁.₅ |
| Al (OH) | SO₄ | or Cl₂ | Al (OH) | (R) | (SO₄)₀.₅ | or Cl |
| Al (OH)₂ | (SO₄)₀.₅ | or Cl | Al (OH)₁.₅ | (R)₀.₅ | (SO₄)₀.₅ | or Cl |

The zirconium-aluminum complex salts according to the invention are manufactured from the stated components in accordance with the relationship implied by the empirical formula.

A particularly simple method of manufacture of these complex salts is to mix about 2 M solutions of the purely inorganic metal salts to which are then successively added, within the limits implied by the empirical formula, 4 M solutions of alkali and of the sodium salts of the abovementioned organic acids. If relatively high proportions of organic acid radicals are added, e.g. 2 moles of sodium propionate/1 mole of metal, the mixtures of the metal salt solutions must be diluted two- to three-fold to remain within the solubility range.

If more alkali is to be added to the mixed metal salt solutions than one of the two metal components can itself tolerate without precipitation, a small proportion of acid radical, e.g. 0.333 mole of propionate/1 mole of metal, must be added before adding the alkali in order to ensure the formation of a complex between the two metal components. If on the other hand the amount of alkali to be used lies within the solubility of the resulting product, it is always more expedient to add the alkali constituent first and the organic acid radical constituent afterwards.

Solutions of such batches may be evaporated or, preferably spray-dried, to give white powders which are readily watersoluble provided the acidity of these solutions is not so great that organic acid is lost. The latter no longer happens if the product contains at least 1 mole of alkali per mole of metal. All solutions of higher acidity must be spray-dried by themselves and may then be mixed with the stated amounts of sodium salt of organic acids and, for example, dolomite. To avoid flying dust from these powders, a dust-binding cationic fat liquor may be added to the solution, in amounts of from about 10 to 20%, by weight, based on product, before spray-drying.

Finally, where necessary, such tanning materials can be brigtened to give a clearer white hue by the conventional method of using very small amounts of chromium salts or blue dyes, of the order of magnitude of from 0.1 to 0.2 percent by weight, based on finished complex salts.

The basic acido-zirconium-aluminum salts thus produced, and preferably having a molar ratio Zr:Al of from 9:1 to 4:6, when used as tanning materials on skins give absolutely boil-resistant leathers with a soft handle resembling that of chrome leather. A pre-condition is that sufficient tanning material should be available relative to skin. This availability differs somewhat for various mixtures and is of the order of magnitude of from 0.05 to 0.10 mole of metal per 100 g of skin.

The minimum availability of tanning material to achieve boil-resistant leather is about 0.05 mole of metal = 0.03 mole of zirconylsulfuric acid and 0.02 mole of aluminum chloride or 0.02 equivalent of aluminum sulfate, when masking with 0.33 –1.0 mole of organic acid radical per mole of metal. The more the mixing ratio deviates from this molar ratio, the higher must be the availability of tanning material in order to give boil-resistant leather.

The tannage itself is carried out by conventional methods. Essentially, the tanning conditions correspond to those of conventional chrome tannage: the delimed pelt is pickled in a short liquor which preferably amounts to about 50% of the pelt weight; a conventional pickling liquor which contains, based on pelt weight, about 6% of sodium chloride or sodium sulfate and about 4% of a suitable pickling acid, especially formic acid or sulfuric acid, has proved advantageous. In general, the pelts are fully pickled after about 2 hours. In difficult cases, say when processing particularly thick pelts, the degree of pickling can be followed by measuring the pH over a cross-section of the pelt. A fully pickled pelt has a uniform pH of 2.5 ± 0.5 over its entire cross-section. In order to carry out the actual tannage, the tanning material, i.e., in the present case, a complex salt according to the invention, or a mixture containing such a salt, is now added, as a solid or as a solution, to the pickling liquor, but it is expedient not to allow the total amount of liquor to increase to more than about 100% of pelts. The tannage is in general allowed to proceed for from 2 to 6 hours in the acid tanning liquor thus obtained; thereafter, where necessary, the alkaline reagent is added as a neutralizing agent, in an amount which gives a constant pH of from 4.2 to 4.6 at the end of the tannage, and the tannage is allowed to proceed for at least a further 6 hours. When using a salt according to the invention, of which the solution gives a pH of from 4.2 to 4.6 from the start, addition of alkaline reagent during tannage is no longer necessary, nor is it necessary when using a self-neutralizing tanning material, e.g. in the form of a mixture of a salt according to the invention and a slow-acting alkaline reagent such as dolomite; in the two last-mentioned cases, the tanning process is allowed to proceed for about 12 hours without further additives.

It is advisable then to place the leather obtained on a horse for 24 hours, after which it is finished conventionally by shaving, dyeing if necessary, and fatliquoring.

In principle, the tannage of fur skins can be carried out in the same way except that usually a longer liquor, amounting to at least 1,000%, based on the material to be tanned, is used. Furthermore it is advisable to have present somewhat more tanning material than in the preferred embodiment of tanning pelts. This is because whilst in tanning pelts it is frequently advantageous to employ the tanning material in an amount corresponding to from 0.05 to 0.07 mole of metal per 100 g of skin, an amount of tanning material corresponding to from 0.07 to 0.09 mole of metal per 100 g of fur skin proves particularly suitable for tanning the latter material.

The fact that the basic acido-zirconium-aluminum salts of the invention are able to produce boil-resistant leather is surprising in as much as the pure metal salt components, used alone, do not give boil-resistant leather. Accordingly, the salts of the invention in this respect give an improvement in the quality of leather which has hitherto only been attainable with chrome tanning materials. In addition, they make it feasible to manufacture chrome-free, boil-resistant, white leather which also has a white cut, and which can be dyed more easily and in brighter hues than can green chrome leather.

EXAMPLE 1

0.1 liter of a 2 M solution of aluminum chloride (483 g of $AlCl_3 . 6 H_2O$ = 102 g of $Al_2O_3$/liter) is added to 0.9 liter of a 2 M solution of zirconylsulfuric acid (760 g of $H_2ZrO(SO_4)_2$, technical grade = 252 g of $ZrO_2$/liter); 0.5 liter of a 2 M sodium carbonate solution (212 g of sodium carbonate/liter) (272 g of sodium formate/liter, 328 g of sodium acetate/liter, 384 g of sodium propionate/liter, 448 g of sodium lactate/liter, 376 g of sodium acrylate/liter and 432 g of sodium methacrylate/liter) are then added to the above mixture, whilst stirring. The complex produced contains zirconium and aluminum in the molar ratio of 9:1 and furthermore contains 1 hydroxyl group per mole of metal and 1 acido radical per mole of metal.

Steeped and delimed skins are pickled with 2 parts by weight of concentrated sulfuric acid and 6 parts by weight of sodium chloride in 70 parts by weight of water. All the tannage data are based on 100 parts by weight of skins. After 1 hour, 60 parts by volume of the above tannage solution are added to the pickling liquor. After a further 6 hours, the liquor is neutralized to pH 4.2 – 4.6, which required about 6.1 parts by weight of dolomite, and tannage is then continued overnight. After completion of tannage, the leather is preferably left on a horse for 24 hours. The leather obtained is pure white, and boil-resistant. It dyes excellently.

EXAMPLE 2

0.5 liter of a 2 M solution of aluminum chloride is added to 1 liter of a 2 M solution of zirconylsulfuric acid and 250 ml of a 4 M sodium propionate solution are then added to the above mixture, whilst stirring. The resulting complex salt contains zirconium and aluminum in the molar ratio of 2:1 and in addition contains 0.33 mole of propionate per mole of metal.

If 35 parts by volume of the above are used as a tanning material per 100 parts by weight of pickled pelts, using the procedure in Example 1, a white boil-resistant leather is obtained. The amount of dolomite required to neutralize the liquor to give a pH of from 4.2 to 4.6 is about 10 parts by weight per 100 parts by weight of pelts.

EXAMPLE 3

1.2 liters of a 1 M solution of aluminum sulfate (666 g of $Al_2(SO_4)_3 . 18 H_2O$ = 102 g of $Al_2O_3$ per liter) are added to 0.8 liter of a 2 M solution of zirconylsulfuric acid. The resulting solution is diluted to 6 liters with water. 2.0 liters of a 4 M solution of sodium formate are then added, whilst stirring. The complex salt formed contains zirconium and aluminum in the molar ratio of 4:6 and also contains 2.0 moles of formate per mole of metal.

If 120 parts by volume of the above are used as a tanning material per 100 parts by weight of pelts, by the method in Example 1, a boil-resistant leather is obtained after 1 day's storage on a horse. The amount of dolomite required to neutralize the tanning liquor to a pH of from 4.2 to 4.6 is about 5.0 parts by weight per 100 parts by weight of pelts.

EXAMPLE 4

0.4 liter of a 1 M aluminum sulfate solution is added to 0.6 liter of a 2 M zirconylsulfuric acid solution, after which 0.5 liter of a 2 M sodium carbonate solution, followed by 0.5 liter of a 4 M sodium propionate solution, are added whilst stirring. After aging for several hours, this solution is spray-dried to give a powder which contains 20.4% and $ZrO_2$ and 5.6% of $Al_2O_3$, corresponding to a molar ratio of zirconium to aluminum of 6:4. In addition, this complex salt contains 1 mole of hydroxyl groups and 1 mole of propionate per mole of metal.

Steeped and bated pelts are pickled with 2 parts of concentrated sulfuric acid and 6 parts of sodium chloride in 100 parts of water. All the tannage data relate to 100 parts of pelts. After 1 hour, 22 parts by weight of the powder described above are added. After a further 6 hours, the liquor is neutralized to pH 4.2 – 4.6, which requires about 5.3 parts by weight of dolomite or 6.1 parts by weight of sodium carbonate or 9.6 parts by weight of sodium bicarbonate. After continuing the tannage overnight and keeping the leather on a horse for 1 day, a white boil-resistant leather is obtained.

EXAMPLE 5

100 parts by weight of the powder prepared according to Example 3 are mixed with 24 parts by weight of dolomite.

The resulting product is a self-neutralizing white mineral tanning material which when employed in an amount of 27.3 parts by weight per 100 parts of pelts, without additional neutralization, gives boil-resistant leathers.

EXAMPLE 6

1 liter of a 2 solution of zirconylsulfuric acid is mixed with 1 liter of a 2 M aluminum chloride solution and the product is spray-dried to give a powder.

The latter contains 28.5% of $ZrO_2$ and 11.8% of $Al_2O_3$, corresponding to a molar ratio of zirconium to aluminum of 1:1.

This powder is employed as a tanning material in accordance with the method described in Example 4, using 13 parts by weight per 100 parts by weight of pelts. However, 3.5 parts by weight of sodium acetate and 6 parts by weight of dolomite are used as neutralizing agents. A white boil-resistant leather is obtained.

EXAMPLE 7

100 parts by weight of the powder prepared according to Example 5 are mixed with 31 parts by weight of sodium propionate and 46 parts by weight of dolomite.

The resulting product is a self-neutralizing white mineral tanning material which when used in an amount of 23 parts by weight per 100 parts by weight of pelts, under the conditions of Example 4, without any neutralization, gives boil-resistant leathers.

EXAMPLE 8

1 liter of a 2 M solution of zirconylsulfuric acid is mixed with 1 liter of a 2 M solution of a 66% basic aluminum chloride (452 g of technical $Al(OH)_2Cl$ = 102 g of $Al_2O_3$ per liter) and this solution is spray-dried to give a powder.

The resulting powder contains 24.6% of $ZrO_2$ and 10.2% of aluminum oxide, corresponding to a molar ratio of zirconium to aluminum of 1:1. In addition, the product contains 1 mole of hydroxyl groups per mole of metal.

100 parts by weight of this powder are mixed with 26.6 parts by weight of sodium propionate (= 0.66 mole of propionate per mole of metal) and with 40 parts by weight of dolomite.

The product may be used as a self-neutralizing white mineral tanning material in an amount of 25 parts by weight per 100 parts by weight of pelts, and under the conditions of Example 4, but without neutralization, gives boil-resistant leathers.

EXAMPLE 9

1 liter of a 2 M zirconylsulfuric acid solution is mixed with 1 liter of a 2 M sodium carbonate solution, whilst stirring, and this mixture is spray-dried to give a powder which contains 33.4% of $ZrO_2$.

100 parts by weight of this powder are then mixed with 61.5 parts by weight of a 66% basic aluminum chloride (a technical product containing 22% of $Al_2O_3$), 40 parts by weight of sodium lactate and 36 parts by weight of dolomite.

This gives a self-neutralizing white mineral tanning material which when used in an amount of 26 parts by weight per 100 parts by weight of pelts gives boil-resistant leathers.

EXAMPLE 10

380 parts by weight of solid zirconylsulfuric acid (a technical product equivalent to 123 parts be weight of $ZrO_2$) are mixed with 226 parts by weight of a 66% basic aluminum chloride (a technical product, equivalent to 51 parts by weight of $Al_2O_3$), 133 parts by weight of sodium propionate and 220 parts by weight of dolomite.

This powder is a self-neutralizing, white mineral tanning material which when used in an amount of 29 parts by weight per 100 parts by weight of pelts, under the conditions in Example 4 but without any neutralization, gives boil-resistant leathers.

EXAMPLE 11

0.5 liter of a 2 M solution of zirconysulfuric acid is mixed with 0.5 liter of a 2 M solution of 66% basic aluminum chloride and 100 parts by weight of propionic acid are added to this mixture. 140 parts by weight of calcium hydroxide, suspended in 1 liter of water, are then added slowly, whilst stirring. The whole is stirred for about 6 hours, until the pH of the solution has risen to 3.5. The solution is then filtered to remove calcium sulfate which has separated out, 100 parts by weight of a cationic fat liquor are then added and the mixture is spray-dried to give a white powder.

The powder thus obtained contains 23.5% of $ZrO_2$ and 9.7% of $Al_2O_3$, corresponding to a molar ratio of zirconium to aluminum of 1:1. In addition, the product contains 2 hydroxyl radicals and 0.66 propionate radical per mole of metal. It is substantially free from sodium sulfate. This powder is mixed with 12.5 parts by weight of dolomite per 100 parts by weight of product.

Steeped and delimed pelts are pickled with 1 part by weight of concentrated sulfuric acid and 6 parts by weight of sodium chloride in 100 parts by weight of water; all the data relating to the tannage are based on 100 parts by weight of pelts. After 1 hours, 18 parts by weight of the above powder mixture are added to the pickling liquor and the tannage is allowed to proceed for 12 hours.

The leather thus obtained is boil-resistant after being kept on a horse for 1 days. Accordingly, the product is a self-neutralizing, white mineral tanning material which, when used on pelts, gives boil-resistant leathers.

EXAMPLE 12

0.5 liter of a 2 M solution of zirconylsulfuric acid is mixed with 0.5 liter of a 1 M solution of aluminum sulfate. 100 parts by weight of propionic acid are added to this mixed solution; 80 parts by weight of sodium carbonate, followed by 175 parts by weight of calcium hydroxide suspended in 1 liter of water, are then added slowly, whilst stirring. The whole is stirred for about 6 hours, until the pH of the solution has risen to 4.5. The solution is then filtered to remove the calcium sulfate which has separated out and the filtrate is spray-dried to give a white powder.

The powder thus obtained contains 29% of $ZrO_2$ and 12% of $Al_2O_2$, corresponding to a molar ratio zirconium to aluminum of 1:1. In addition, the product contains 2

1 moles of hydroxyl groups and 0.66 mole of the propionate radicals per mole a metal. It is substantially free from neutral salt.

Using 12 parts by weight of the above product per 100 parts by weight of pelts, under the conditions mentioned in Example 11, a white boil-resistant leather is obtained. Accordingly, the product is a single-complex white mineral tanning material which, when used to treat pelts under the conditions described, requires no neutralization and gives boil-resistant leathers.

We claim:

1. In a process for tanning skins and hides by treating the delimed and pickled skins and hides with an acid aqueous solution of a mineral tanning agent at a pH which is from 4.2 to 4.6 at the end of the treatment, the improvement which comprises using as the mineral tanning agent a complex salt of empirical formula $$[(ZrO)_a(Al)_b(OH)_c(R)_d(X)_f] H_e,$$

in which R is a monocarboxylic acid radical of 1 to 4 carbon atoms, X is chloride or half of sulfate, $a$ and $b$ are independently of each other from 1 to 9, $c$ is from 0 to $((4a+3b)-0.333(a+b))$ and $d$ is from $0.333(a+b)$ to $((4a+3b)-0.333(a+b))$, provided $c+d$ is from $0.333(a+b)$ to $(4a+3b)$, $f$ is $(4a+3b)-(c+d)$ and $e$ is $2a$.

2. A process as claimed in claim 1 wherein the amount of said complex salt is sufficient to provide at least 0.03 mole of zirconium per 100 g of skin or hide and 0.02 mole of aluminum per 100 g of skin or hide.

3. A process as claimed in claim 1 wherein zirconium and aluminum are present in said complex salt in the molar ratio of from 4:6 to 9:1.

4. A process as claimed in claim 1 wherein $c$ is in the range of 0 to $(3a+2b)$.

5. A process as claimed in claim 1 wherein $d$ is from $0.333(a+b)$ to $(3a+2b)$.

6. A process as claimed in claim 1 wherein $c+d$ equals $3a+2b$.

7. A process as claimed in claim 1, wherein zirconium and aluminum are present in said complex salt in a molar ratio of from 4:6 to 9:1, $c$ is from 0 to $(3a+2b)$, $d$ is from $0.333(a+b)$ to $(3a+2b)$ and $c+d = 3a+2b$.

8. A process as claimed in claim 1, wherein $c$ is from 0 to $(3a+2b)$, $d$ is from $0.333(a+b)$ to $(3a+2b)$ and $c+d = 3a+2b$.

9. A process as claimed in claim 1, wherein $c$ is from 0 to $(3a+2b)$, $d$ is from $0.333(a+b)$ to $(3a+2b)$ and $c+d = 3a+2b$, and R is the monocarboxylic acid radical of formic acid, acetic acid, propionic acid, lactic acid, acrylic acid or methacrylic acid.

10. A process as claimed in claim 1, wherein $a$ is the monocarboxylic acid radical of formic acid, acetic acid, propionic acid, lactic acid, acrylic acid or methacrylic acid.

* * * * *